United States Patent [19]
Komatsu et al.

[11] Patent Number: 5,528,648
[45] Date of Patent: Jun. 18, 1996

[54] METHOD AND APPARATUS FOR ANALYZING CONTAMINATIVE ELEMENT CONCENTRATIONS

[75] Inventors: Fumio Komatsu, Fuchu; Kunihiro Miyazaki, Tokyo; Ayako Shimazaki, Yokohama, all of Japan

[73] Assignee: Kabushiki Kaisha Toshiba, Kawasaki, Japan

[21] Appl. No.: 348,929

[22] Filed: Nov. 25, 1994

[30] Foreign Application Priority Data

Nov. 25, 1993 [JP] Japan .................................. 5-295473

[51] Int. Cl.⁶ .................................................. G01N 23/223
[52] U.S. Cl. .................................................. 378/45; 378/210
[58] Field of Search .......................................... 378/45–49

[56] References Cited

U.S. PATENT DOCUMENTS

| 5,422,925 | 6/1995 | Komatsu et al. | 378/45 |
| 5,430,786 | 7/1995 | Komatsu et al. | 378/45 |

*Primary Examiner*—Craig E. Church
*Attorney, Agent, or Firm*—Oblon, Spivak, McClelland, Maier & Neustadt

[57] ABSTRACT

The fluorescent X-ray generated by elements when an X-ray is total reflected from a substrate surface is detected by a fluorescent X-ray detecting circuit; the fluorescent X-ray peak generated by the substrate element and the fluorescent X-ray peaks generated by contaminative elements are separated by a peak separating circuit; an integral intensity $I_0$ of the fluorescent X-ray peak generated by the substrate element and integral intensities I of the fluorescent X-ray peaks generated by the contaminative elements are calculated by an integral intensity calculating circuit, respectively; and contaminative element concentrations $N=N_0 \cdot (\eta_0 / I_0) \cdot (I / \eta)$ (where $N_0$ denotes the surface concentration of the substrate; $\eta_0$ denotes the fluorescent yield of the substrate; and $\eta$ denotes the fluorescent yield of the contaminative elements) are calculated by a contaminative element concentration calculating circuit on the basis of the calculated integral intensities $I_0$ and I. The contaminative elements can be analyzed non-destructively without use of any analytical curves, so that it is possible to save much labor required to prepare the analytical curves.

5 Claims, 6 Drawing Sheets

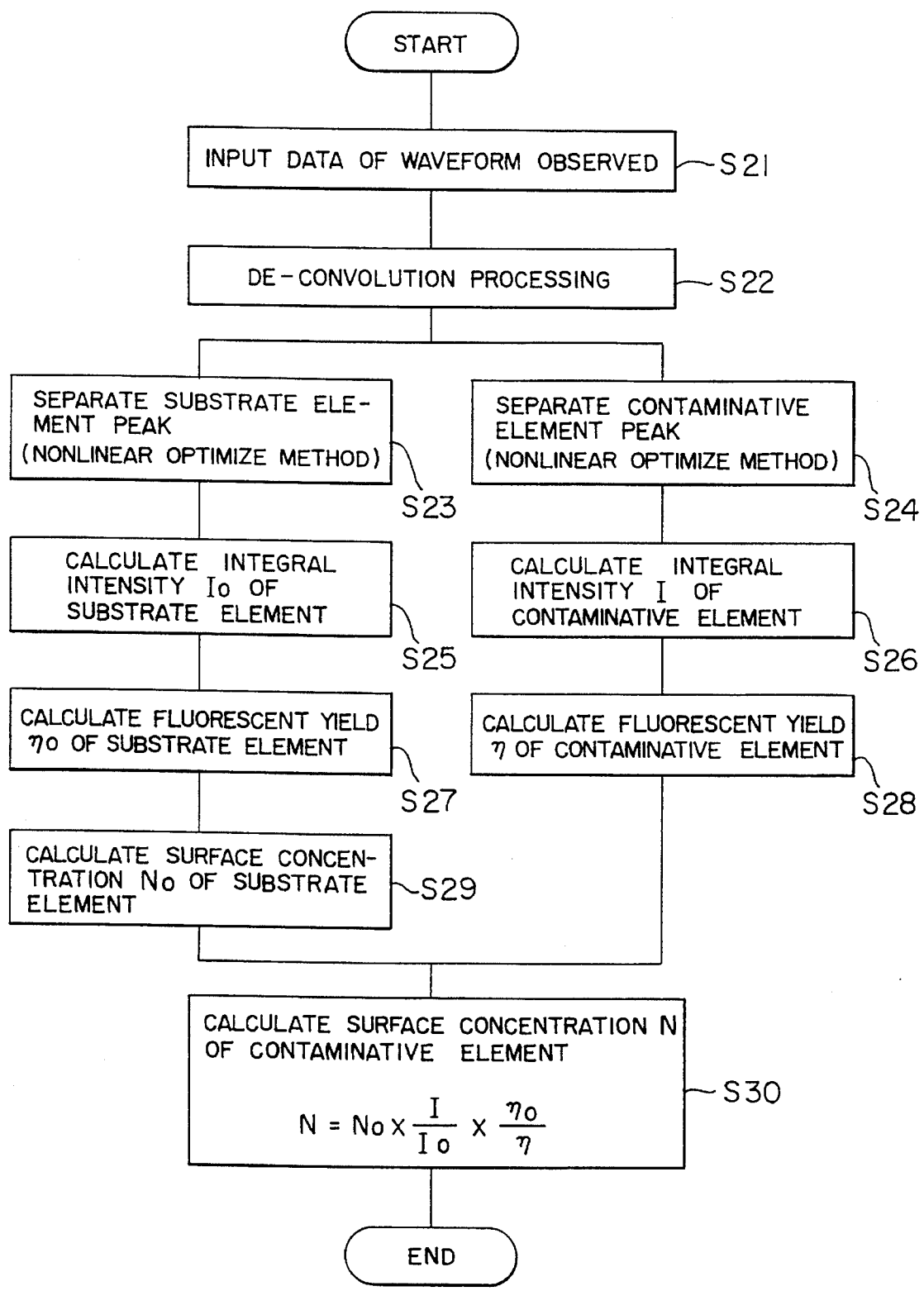
F I G. 2

METHOD AND APPARATUS FOR ANALYZING CONTAMINATIVE ELEMENT CONCENTRATIONS

BACKGROUND OF THE INVENTION

1. Field of the Invention

The present invention relates to a method and an apparatus for analyzing contaminative element concentrations, and more specifically to a method and an apparatus for measuring contaminative element concentrations on a semiconductor substrate, for instance with the use of an energy dispersive type total reflection X-ray fluorescence analysis.

2. Description of the Background Art

Conventionally, as a non-destructive contaminative element concentration analyzing apparatus, there is so far known a total reflection X-ray fluorescence analysis (see "Inspection, Analysis and Measurement Technology Required 16M/64M Integration or After", by Ayako SIMAZAKI, Kunihiro MIYAZAKI; NIKKEI MICRODEVICE, No. 86, pages 148, 154, 156 and 158, Aug., 1992). Furthermore, as a contaminative element concentration analyzing apparatus based upon total reflection X-ray fluorescence analysis, an energy or wavelength dispersive type apparatus is known. Since the contaminative element concentrations can be analyzed nondestructively with the use of the contaminative element concentration analyzer based upon the total reflection X-ray fluorescence analysis, it has become possible to manage the contamination of silicon wafer during the semiconductor manufacturing process, and thereby the contamination of wafer can be reduced effectively.

FIG. 5 is a conceptual block diagram showing an example of the contaminative element concentration analyzer using the energy dispersive type total reflection X-ray fluorescence analysis.

In FIG. 5, a sample supporting base 42 is mounted within a vacuum chamber 41, and a sample (e.g., silicon wafer) 43 is mounted on this sample base 42. An X-ray generated by a rotating pair-cathode type X-ray source 44 is converted to a monochromatic ray through a monochrometer 45, being passed through a slit 49, and then allowed to be incident upon the sample 43 at a small total-reflection angle. On the basis of this incident X-ray, a fluorescent X-ray can be generated from the surface of the sample 43. The generated fluorescent X-ray is detected by a detector (e.g., semiconductor detector ), and converted into electric signals corresponding thereto. The fluorescent X-ray signals detected as described above are processed by pulse processor 47 to obtain an observed waveform as shown in FIG. 6. In FIG. 6, the abscissa designates the energy of the detected fluorescent X-ray and the ordinate designates the signal intensity (relative intensity according to the number of photons incident upon the detector 46) of the detected fluorescent X-ray. FIG. 6 indicates that the observed waveform (graph) has peeks each of which has a value for each element (silicon and other contaminative elements) contained in the silicon wafer 43. In addition, the integral intensity (which corresponds to an area of a peak waveform) of each peak is proportional to the concentration of the element.

On the other hand, an arithmetic processing circuit 48 stores information indicative of the relationship between the integral intensity of the fluorescent X-ray and the concentration for each contaminative element, which referred to as "analytical curve". Therefore, the arithmetic processing circuit 48 first separates the peaks of the contaminative elements from the observed waveform (see FIG. 6) inputted by the pulse processor 47 for concentration detection, and then calculates the respective integral intensities of the separated peaks, and obtains the contaminative element concentrations on the basis of the integral intensities and the analytical curves.

A co-pending U.S. patent application 08/116,750 which is incorporated herein discloses a method of peak separation.

Here, the analytical curves have been so far prepared by actually measuring the contaminative element concentrations and the fluorescent X-ray intensity distribution (see FIG. 3). In more detail, the concentrations of predetermined contaminative elements are measured, and further the fluorescent X-ray distribution (see FIG. 3) of the same sample is detected. Further, each peak integral intensity is calculated, and the relationship between each contaminative element concentration and each integral intensity is plotted so as to form a graph (the ordinate: concentrations; abscissa: integral intensities) to prepare the analytical curve. Here, the concentrations of the contaminative elements can be measured in accordance with a destructive analysis, for instance using WSA (Wafer Surface Analysis) and AAS (Atomic Absorption Spectrometry) (see AAS: by A. Simazaki, ECS Proceedings, Defects in silicon II, Ed. M. Bullis et el., pp. 47, 1991).

In the conventional contaminative element concentration analyzer as shown in FIG. 5, however, since it has been necessary to form the analytical curves for respective contaminative elements, there exists such a problem in that it takes much labor to from the various analytical curves of various elements.

Furthermore, in the case of the atomic absorption spectrometry, since the element concentration must be measured only for each element, when the analytical curves of a number of different contaminative elements are required to form, it has been necessary to use the recovery solution obtained by the wafer surface analysis, after having been divided. Therefore, in the case of low concentration (less than $10^9$ atoms/cm$^2$), since there exists a possibility that the measurement results disperse, the number of plots must be increased to obtain an accurate analytical curve, so that it takes much labor to prepare the analytical curve from this point of view.

Furthermore, since the intensity of the fluorescent X-ray detected by the detector 46 is of relative value, the relationship between the integral value of the fluorescent X-ray intensity and the element concentration is susceptible to the optical system. That is, when the optical system changes, the relationship between the tow also changes, with the result that the conventional contaminative element concentration analyzer involves such drawbacks that the analytical curves must be prepared again whenever the optical system is modified due to repair, for instance.

SUMMARY OF THE INVENTION

Accordingly, the object of the present invention is to provide a method and an apparatus for analyzing the contaminative element concentrations non-destructively without use of any analytical curves.

According to the present invention, there is provided a method of analyzing contaminative element concentrations on a substrate surface on the basis of energy dispersive type total reflection X-ray spectroscopy, comprising the steps of:

irradiating an X-ray upon a substrate to be analyzed at a predetermined incident angle;

detecting a fluorescent X-ray generated by elements when the irradiated X-ray is total reflected from the substrate surface to be analyzed, to obtain an observed waveform;

separating a peak of an element of the substrate and peaks of contaminative elements to be analyzed from each other in accordance with non-linear optimization method;

discriminating the peak of the substrate element and the peaks of contaminative elements to be analyzed from each other, to obtain an integral intensity $I_0$ of the substrate element peak and integral intensities I of contaminative element peaks;

calculating a fluorescent yield $\eta_0$ of the substrate element and fluorescent yields $\eta$ of contaminative elements on the basis of atomic numbers corresponding thereto, respectively; and calculating surface atomic concentrations of the contaminative elements to be analyzed on the basis of the calculated integral intensities $I_0$ and I, the fluorescent yields $\eta_0$ and $\eta$, and a substrate surface contaminative element concentration $N_0$, and in accordance with the following formula:

$N = N_0 \cdot (\eta_0 / I_0) \cdot (I / \eta)$

According to the another aspect of the invention, there is provided a contaminative element concentration analyzing apparatus, comprising:

X-ray irradiating means for irradiating an X-ray upon a substrate to be analyzed at a predetermined incident angle;

X-ray detecting means for detecting a fluorescent X-ray generated by elements when the irradiated X-ray is total reflected from a surface of the substrate, to obtain an observed waveform;

peak separating means for separating a peak of the fluorescent X-ray generated by the substrate element and peaks of the fluorescent X-ray generated by contaminative elements from each other on the basis of the fluorescent X-ray waveform detected by said X-ray detecting means;

integral intensity calculating means for calculating an integral intensity $I_0$ of the fluorescent X-ray peak generated by the substrate element and integral intensities I of the fluorescent X-ray peaks generated by the contaminative elements, respectively on the basis of the separated peaks; and contaminative element concentration calculating means for calculating contaminative element concentrations in accordance with $N = N_0 \cdot (\eta_0 / I_0) \cdot (I / \eta)$ on the basis of the integral intensities $I_0$ and I calculated by said integral intensity calculating means.

According to the present invention, there exists such an advantage that contaminative elements can be analyzed non-destructively, without use of any analytical curves, at such a high precision as with the case of the conventional analyzing apparatus. In addition, since the concentration of the substrate itself element is analyzed for each substrate, it is possible to prevent the measurement error caused by measurement fluctuations.

BRIEF DESCRIPTION OF THE DRAWINGS

In the attached drawings:

FIG. 2 is a flowchart for assistance in explaining the procedure of the contaminative element concentration analyzing method according to the present invention;

DETAILED DESCRIPTION OF THE PREFERRED EMBODIMENTS

First, the principle of the present invention will be described.

The inventors have newly found that there exists a relationship between the surface concentration $N_0$ (atoms/cm$^2$) of the substrate element and the concentrations N of the contaminative elements in the substrate as follows:

$N (\eta / I) = N_0 \cdot (\eta_0 / I_0)$ where $I_0$: Integral intensity of fluorescent X-ray generated by substrate I: Peak integral intensity of the fluorescent X-ray generated by contaminative element $\eta_0$: Fluorescent yield of substrate element $\eta$: Fluorescent yield of contaminative element Here, the surface concentration $N_0$ of the substrate element can be obtained through calculations when the crystal structure and the orientation thereof are known. Further, the fluorescent yields $\eta_0$ and $\eta$ of the substrate and the contaminative elements can be obtained through calculations when the atomic numbers are known.

Accordingly, it is possible to obtain the contaminative element concentrations N by detecting the fluorescent X-ray waveform by fluorescent X-ray detecting means; by separating the peak of the fluorescent X-ray generated by the substrate and the peaks of the fluorescent X-ray generated by the contaminative elements from each other on the basis of the detected waveform by peak separating means; by calculating these peak integral intensities $I_0$ and I by integral intensity calculating means; and by calculating contaminative element concentrations on the basis of the calculated integral intensities $I_0$ and I and in accordance with the above-mentioned formula by contaminative element concentration calculating means.

An embodiment of the present invention will be described hereinbelow by taking the case where contaminative elements on the (100) surface of a silicon wafer (as the substrate to be measured) are analyzed.

Figure 1:
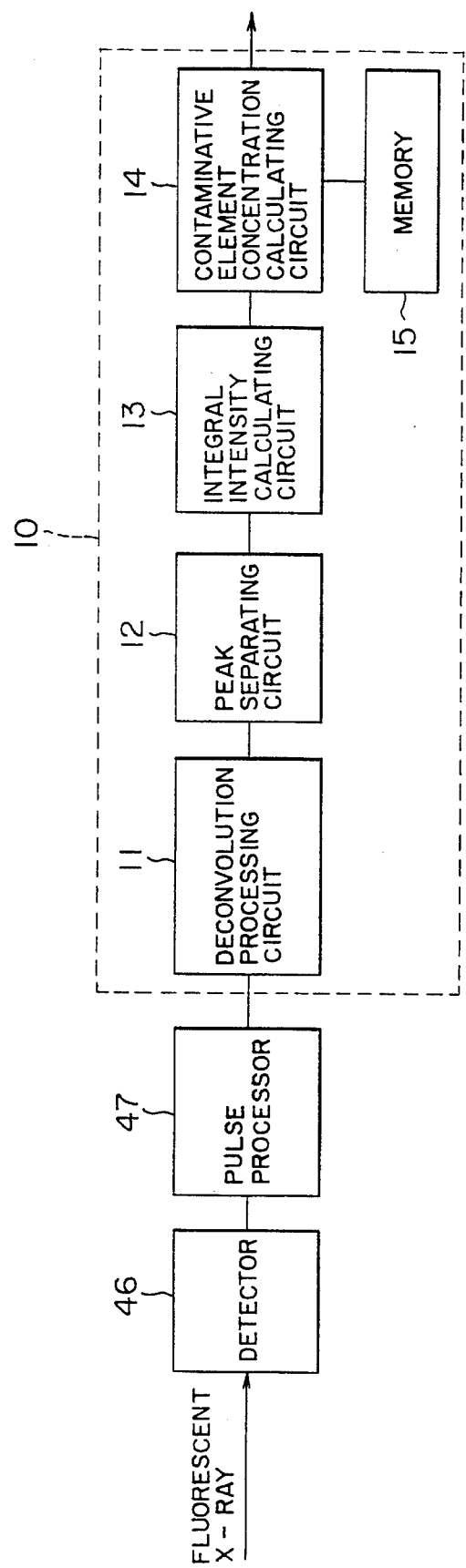
FIG. 1 is a block diagram showing a detector and an arithmetic processing circuit of an embodiment of the contaminative element concentration analyzing apparatus according to the present invention, by which the contaminative element concentration analyzing method according to the present invention can be realized.
Figure 3:
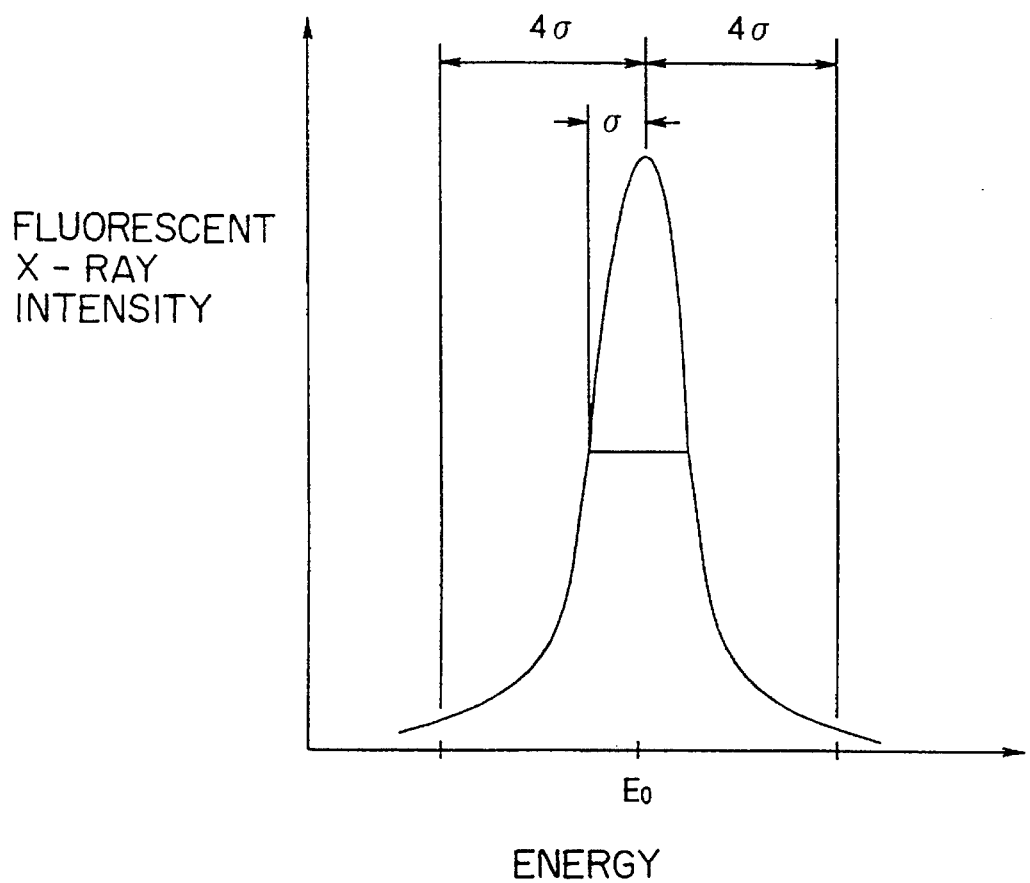
FIG. 3 is a conceptual graphical representation for assistance in explaining the integrating method in the integral intensity calculating circuit shown in FIG. 1.

FIG. 1 is a block diagram showing a detector and an arithmetic processing circuit of the contaminative element concentration analyzing apparatus according to the present invention. FIG. 2 is a flowchart showing the contaminative element concentration analyzing method using the same analyzing apparatus.

Figure 5:
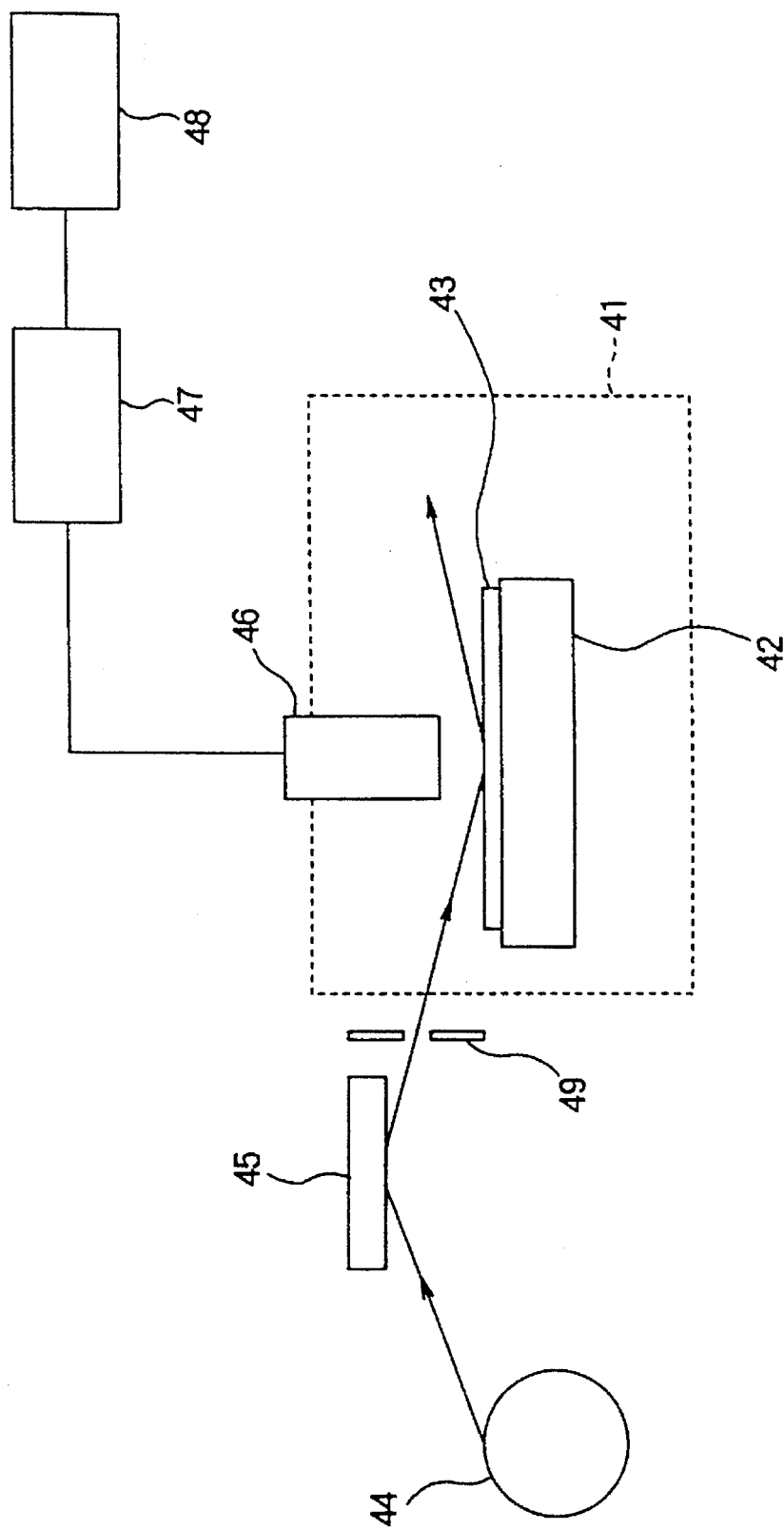
FIG. 5 is a conceptual block diagram showing an example of the conventional contaminative element concentration analyzing apparatus.

FIG. 1 shows only the processing section after the detector 46 shown in FIG. 5. The construction other than those shown in FIG. 1 is the same as that shown in FIG. 5. Further, only the procedure executed by the arithmetic processing circuit 10 of the present invention differs from that executed by the arithmetic processing circuit 48 shown in FIG. 5.

Figure 6:
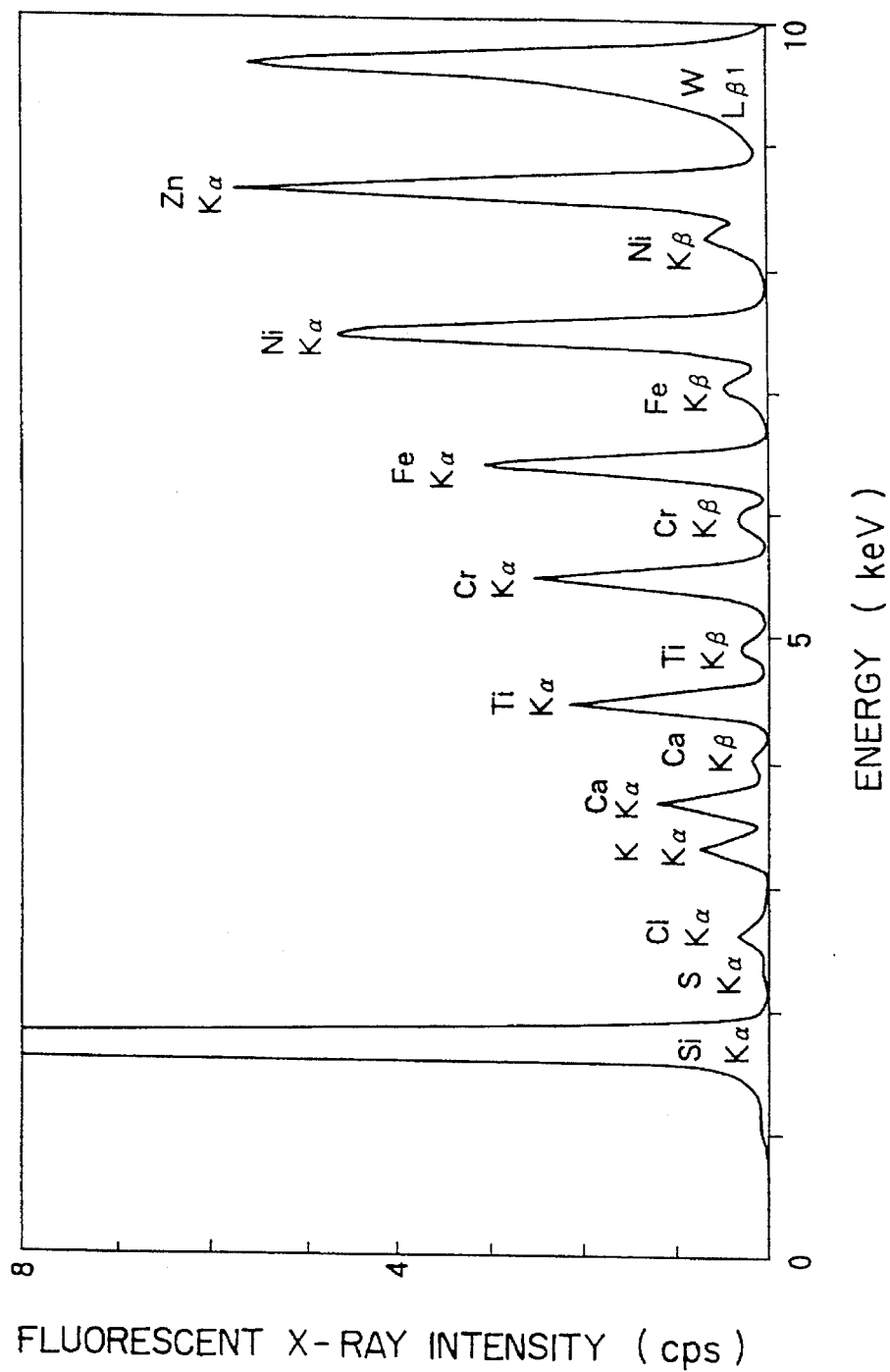
FIG. 6 is a graphical representation showing the observed waveform outputted by the pulse processor shown in FIG. 5.

The fluorescent X-ray generated from the surface of the silicon water 43 is allowed to be incident upon a detector (which corresponds to fluorescent X-ray detecting means of the present invention) 46 for instance such as a semiconductor detector. The detector 46 converts the intensity of the incident fluorescent X-ray into electric signal levels, and outputs the converted signal levels. The signal levels are inputted to a pulse processor 47 to obtain the observed waveform in the same way as with the case of the conventional case (see FIG. 6).

The obtained observed waveform is inputted to a de-convolution processing circuit 11 of the arithmetic processing circuit 10 (in step S21) for de-convolution processing (in step S22). This de-convolution processing is necessary to improve the distortion of the observed waveform by executing an approximate operation in accordance with Gaussian function on the basis of an apparatus function based upon the energy resolution of the detector 46, for instance.

The observed waveform to which the de-convolution processing has been executed is inputted to a peak separating circuit 12 to separate the peak of the silicon (in step S23) and the peaks of the contaminative elements (whose concentrations are to be detected) (in step S24) from the inputted observed waveform. Here, as the method of separating the peaks from the observed waveform, a method of approximating the peaks in accordance with non-linear optimization method (by use of Gaussian function) has been adopted.

The respective peak data separated as described above are inputted to an integral intensity calculating circuit 13. The integral intensity calculating circuit 13 calculates the integral intensity $I_0$ of the peak of silicon and the integral intensities I of the peaks of contaminative elements (in step S25 and S26). To calculate the integral intensities $I_0$ and I, the waveform curve is integrated within the range of $\pm 4\sigma$ on both sides of the position $E_0$ at which the waveform reaches a maximum value, where $\sigma$ represents a deviation from the position $E_0$ at a half value of the peak value (ordinate) in the distribution curve (referred to as a half width of half maximum). The calculated integral intensities $I_0$ and I are transmitted to a contaminative element concentration calculating circuit 14.

The contaminative element concentration calculating circuit 14 calculates the contaminative element concentration N on the basis of the surface concentration $N_0$, the fluorescent yield $\eta_0$ of the silicon wafer, the fluorescence yield $\eta$ of the contaminative element all previously calculated in steps S27 to S29 and stored in a memory 15 (in step S30).

Here, the (100) surface of the silicon is of face-centered cubic lattice, so that the number of surface atoms is two; the number of atoms within the most proximity interatomic distance (2.35 angstrom) is two; and the lattice constant is 5.431 angstrom. Therefore, $$N_0 = 4 / (5.431 \times 10^{-8})^2 = 1.355 \times 10^{15} \ (atoms/cm^2)$$

Further, when the atomic number is z, the fluorescent yield $\eta (\eta_0$ or $\eta)$ can be obtained as $$\eta = (a+bz+cz^3)^4 / \{1+(a+bz+cz^3)^4\}$$

where a, b and c are constants determined for each element, and these values of silicon are given as follows (See J. W. Robinson: "Handbook of Spectroscopy", Vol. 1, CRC Press, 1974):

a=−0.038 b=0.034 c=0.116×10⁻⁶

Therefore, the fluorescent yield $\eta$ of the silicon is 0.047; the fluorescent yield $\eta$ of a contaminative element Fe is 0.347, and that of Ni is 0.414, for instance.

The contaminative element concentration calculating circuit 14 executes the following calculation by inputting the integral intensities $I_0$ and I from the integral intensity calculating circuit 13 and the stored data $N_0$, $\eta_0$ and $\eta$ from the storage section 15:

$$N = N_0 \cdot (\eta_0 / I_0) \cdot (I / \eta)$$

with the result that it is possible to calculate the surface concentration N of each of the contaminative elements (in step S30).

Figure 4:
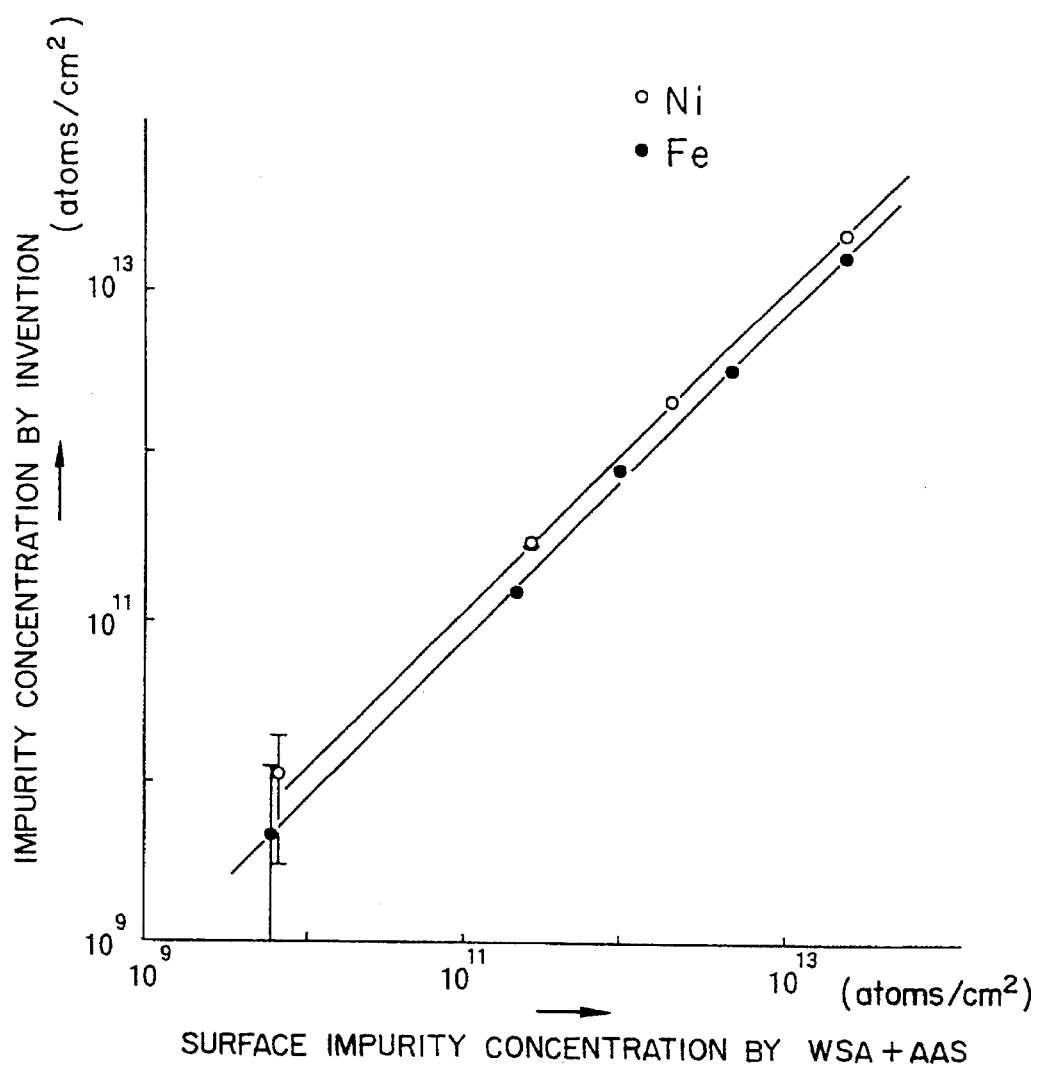
FIG. 4 is a graphical representation for assistance in explaining the comparison in concentration analysis precision between the contaminative element concentration analyzing apparatus shown in FIG. 1 and the combination of the wafer surface analysis (WSA) and the atomic absorption spectrometry (AAS)

FIG. 4 is a graphical representation for comparison of the precision of concentration analysis between the contaminative element concentration analyzing apparatus shown in FIG. 1 and the combination of WSA (wafer surface analysis) and AAS (atomic absorption spectrometry), in which the ordinate designates the concentrations analyzed by the apparatus according to the present invention and the abscissa designates the concentrations analyzed by the combination of WSA and AAS. Further, in FIG. 4, white dots indicate contaminative element Fe and block dots indicate contaminative element Ni.

FIG. 4 indicates that the concentration analysis results of the analyzing apparatus according to the present invention well match the concentration analysis results of the combination of WSA and AAS at a high precision, and further the correlation between both can be maintained even when the concentration is less than $10^9/cm^2$. As described above, FIG. 4 indicates that the contaminative element concentration analyzing apparatus according to the present invention can obtain as high a concentration analysis precision as that of the conventional contaminative element concentration analyzing apparatus.

Further, in this embodiment, the integral intensity $I_0$ of the silicon has been obtained whenever the silicon wafer is changed. Therefore, even if two sample bases 42 (see FIG. 5) are dislocated and thereby the measuring conditions fluctuate, since the ratio of $I_0$ to I does not change, it is possible to prevent the occurrence of the measurement error.

Further the embodiment has been explained by taking the case where the concentrations of contaminative elements of the silicon (100) surface are analyzed. Without being limited to only the silicon (100) surface, it is of course possible to analyze the concentrations of elements on other surfaces of other materials in the same way as described above.

Further, in the present embodiment, the apparatus circuit is composed of hardware such as the peak separating means, the integral intensity calculating means, the contaminative element concentration calculating means, and the de-convolution processing means. Without being limited to only hardware construction, it is also possible to use a microprocessor as the arithmetic processing circuit 48 and to execute a part of or all of the similar operation in accordance with software procedure.

As described above, in the contaminative element concentration analyzing apparatus according to the present invention, there exists such an advantage that contaminative elements can be analyzed non-destructively, without use of any analytical curves, at such a high precision as with the case of the conventional analyzing apparatus. In addition, since the concentration of the substrate itself element is analyzed for each substrate, it is possible to prevent the measurement error caused by measurement fluctuations.

What is claimed is:

1. A method of analyzing contaminative element concentrations on a substrate surface on the basis of energy decentralization type total reflection X-ray spectroscopy, comprising the steps of:

irradiating an X-ray upon a substrate to be analyzed at a predetermined incident angle;

detecting a fluorescent X-ray generated by elements when the irradiated X-ray is total reflected from the substrate surface to be analyzed, to obtain an observed waveform;

separating a peak of an element of the substrate and peaks of contaminative elements to be analyzed from each other in accordance with non-linear optimization method;

discriminating the peak of the substrate element and the peaks of contaminative elements to be analyzed from each other, to obtain an integral intensity $I_0$ of the substrate element peak and integral intensities I of contaminative element peaks;

calculating a fluorescent yield $\eta_0$ of the substrate element and fluorescent yields $\eta$ of contaminative elements on the basis of atomic numbers corresponding thereto, respectively; and calculating surface atomic concentrations of the contaminative elements to be analyzed on the basis of the calculated integral intensities $I_0$ and I, the fluorescent yields $\eta_0$ and $\eta$, and a substrate surface contaminative element concentration $N_0$, and in accordance with the following formula:

$N = N_0 \cdot (\eta_0 / I_0) \cdot (I / \eta)$

2. The method of analyzing contaminative element concentrations on a substrate surface according to claim 1, which further comprises the step of executing de-convolution processing of the waveform by use of an apparatus function determined on the basis of energy resolution of a fluorescent X-ray detector, to improve waveform distortion, before separating the peaks.

3. The method of analyzing contaminative element concentrations on a substrate surface according to claim 1, wherein said integral intensities $I_0$ and I are calculated by performing integration for range of four half widths of half maximum.

4. A contaminative element concentration analyzing apparatus, comprising:

X-ray irradiating means for irradiating an X-ray upon a substrate to be analyzed at a predetermined incident angle;

X-ray detecting means for detecting a fluorescent X-ray generated by elements when the irradiated X-ray is total reflected from a surface of the substrate, to obtain an observed waveform;

peak separating means for separating a peak of the fluorescent X-ray generated by the substrate element and peaks of the fluorescent X-ray generated by contaminative elements from each other on the basis of the fluorescent X-ray waveform detected by said X-ray detecting means;

integral intensity calculating means for calculating an integral intensity $I_0$ of the fluorescent X-ray peak generated by the substrate element and integral intensities I of the fluorescent X-ray peaks generated by the contaminative elements, respectively on the basis of the separated peaks; and contaminative element concentration calculating means for calculating contaminative element concentrations in accordance with $N = N_0 \cdot (\eta_0 / I_0) \cdot (I / \eta)$ where $N_0$: surface concentration of the substrate $\eta_0$: fluorescent yield of the substrate $\eta$: fluorescent yield of the contaminative element on the basis of the integral intensities $I_0$ and I calculated by said integral intensity calculating means.

5. The contaminative element concentration analyzing apparatus of claim 4, which further comprises de-convolution processing means for executing de-convolution processing of the fluorescent X-ray waveform detected by said fluorescent X-ray detecting means by use of an apparatus function determined on the basis of energy resolution of said fluorescent X-ray detecting means, before the waveform peaks are separated by said peak separating means.

* * * * *